United States Patent [19]

Guadiana

[11] Patent Number: 5,365,956
[45] Date of Patent: Nov. 22, 1994

[54] TOOTHBRUSH AND DENTAL FLOSS HOLDER

[76] Inventor: Gregorio G. Guadiana, 41 Hiran, Nacogdoches, Tex. 75961

[21] Appl. No.: 179,389

[22] Filed: Jan. 10, 1994

[51] Int. Cl.5 ............................................. A45D 44/18
[52] U.S. Cl. .................................... 132/309; 132/311; 132/324; 132/325; 132/326
[58] Field of Search ............... 132/308, 309, 311, 323, 132/324, 325, 326, 327

[56] References Cited

U.S. PATENT DOCUMENTS

| | | | |
|---|---|---|---|
| 301,055 | 6/1884 | Greene | 132/325 |
| 1,488,214 | 3/1924 | Mason | 132/324 |
| 1,537,853 | 5/1925 | Mason | 132/309 |
| 2,233,936 | 3/1941 | Campbell | 132/325 |
| 2,517,806 | 8/1950 | Streiler | 132/309 |
| 3,939,853 | 2/1976 | Spanondis | 132/309 |
| 4,016,891 | 4/1977 | Kupperman et al. | 132/309 |
| 5,097,852 | 3/1992 | Wu | 132/309 |

*Primary Examiner*—Gene Mancene
*Assistant Examiner*—Frank A. LaViola
*Attorney, Agent, or Firm*—Gary Alan Culliss

[57] ABSTRACT

A toothbrush having a spool of floss stored within the handle and a floss holding frame for holding a portion of the floss in a taut condition for use thereof. The toothbrush includes a handle which terminates in a floss holding frame across which floss from the spool may be extended and held tight. The floss spool and the floss holding frame are longitudinally arranged such that a protective cover may be placed thereover.

6 Claims, 3 Drawing Sheets

TOOTHBRUSH AND DENTAL FLOSS HOLDER

BACKGROUND OF THE INVENTION

1. Field of the Invention

The present invention relates to dental care devices and more particularly pertains to a toothbrush and dental floss holder having a spool of floss stored within the handle and a floss holding frame for holding a portion of the floss in a taut condition for use thereof.

2. Description of the Prior Art

The use of dental care devices is known in the prior art. More specifically, dental care devices heretofore devised and utilized for the purpose of brushing and flossing are known to consist basically of familiar, expected and obvious structural configurations, notwithstanding the myriad of designs encompassed by the crowded prior art which have been developed for the fulfillment of countless objectives and requirements.

For example, a tamper resistant disposable toothbrush and flossing device is illustrated in U.S. Pat. No. 5,184,719 which includes a toothbrush having a flossing device located at a distal end of the handle. The flossing device comprises fork-like prongs between which is mounted a free span of floss under tension. If desired, the handle is sufficiently flexible such that it may be bent back to enable the dentifrice-coated brush to contact the floss and apply some of the dentifrice thereto.

A combination toothbrush and dental floss holder is disclosed in U.S. Pat. No. 4,887,621 which includes a detachable toothbrush and a cavity for receiving a spool of dental floss. A removable screw cap covers and protects the cutting blade and dental floss.

Another patent of interest is U.S. Pat. No. 4,016,891 which describes a dental floss holder for detachable securement to a toothbrush handle or the like. The dental floss holder comprises a fork member having a pair of spaced arms across which a dental floss strip of a prescribed length is strung. The extension is adapted to be detachably secured to the end of a handle forming a part of a toothbrush.

Other known prior art dental care devices include U.S. Pat. Nos. 5,040,553, and 5,078,526.

While these devices fulfill their respective, particular objectives and requirements, the aforementioned patents do not disclose a toothbrush and dental floss holder having a spool of floss stored within the handle and a floss holding frame for holding a portion of the floss in a taut condition for use thereof. Furthermore, none of the known prior art dental care devices teach or suggest a toothbrush and dental floss holder comprising the aforementioned structure, wherein the floss holding frame and the floss spool are longitudinally aligned such that a protective cover may be placed thereover.

In these respects, the toothbrush and dental floss holder according to the present invention substantially departs from the conventional concepts and designs of the prior art, and in so doing provides an apparatus primarily developed for the purpose of supporting a spool of floss within the handle of a toothbrush adjacent a floss holding frame across which a portion of the floss may be positioned for use.

SUMMARY OF THE INVENTION

In view of the foregoing disadvantages inherent in the known types of dental care devices now present in the prior art, the present invention provides a new toothbrush and dental floss holder construction wherein the same can be utilized for brushing teeth, storing dental floss, and holding a length of floss in a taut condition for use thereof. As such, the general purpose of the present invention, which will be described subsequently in greater detail, is to provide a new toothbrush and dental floss holder apparatus which has many of the advantages of the dental care devices mentioned heretofore and many novel features that result in a toothbrush and dental floss holder which is not anticipated, rendered obvious, suggested, or even implied by any of the prior art dental care devices, either alone or in any combination thereof.

To attain this, the present invention generally comprises a toothbrush having a spool of floss stored within the handle and a floss holding frame for holding a portion of the floss in a taut condition for use thereof. The toothbrush includes a handle which terminates in a floss holding frame across which floss from the spool may be extended and held tight. The floss spool and the floss holding frame are longitudinally arranged such that a protective cover may be placed thereover.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new toothbrush and dental floss holder apparatus which has many of the advantages of the dental care devices mentioned heretofore and many novel features that result in a toothbrush and dental floss holder which is not anticipated, rendered obvious, suggested, or even implied by any of the prior art dental care devices, either alone or in any combination thereof.

It is another object of the present invention to provide a new toothbrush and dental floss holder which may be easily and efficiently manufactured and marketed.

It is a further object of the present invention to provide a new toothbrush and dental floss holder which is of a durable and reliable construction.

An even further object of the present invention is to provide a new toothbrush and dental floss holder which is susceptible of a low cost of manufacture with regard to both materials and labor, and which accordingly is then susceptible of low prices of sale to the consuming public, thereby making such toothbrush and dental floss holders economically available to the buying public.

Still yet another object of the present invention is to provide a new toothbrush and dental floss holder which provides in the apparatuses and methods of the prior art some of the advantages thereof, while simultaneously overcoming some of the disadvantages normally associated therewith.

Still another object of the present invention is to provide a new toothbrush and dental floss holder having a spool of floss stored within the handle and a floss holding frame for holding a portion of the floss in a taut condition for use thereof.

Yet another object of the present invention is to provide a new toothbrush and dental floss holder of the aforementioned structure in which the floss spool and the floss holding frame are longitudinally aligned such that a protective cover may be placed thereover.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
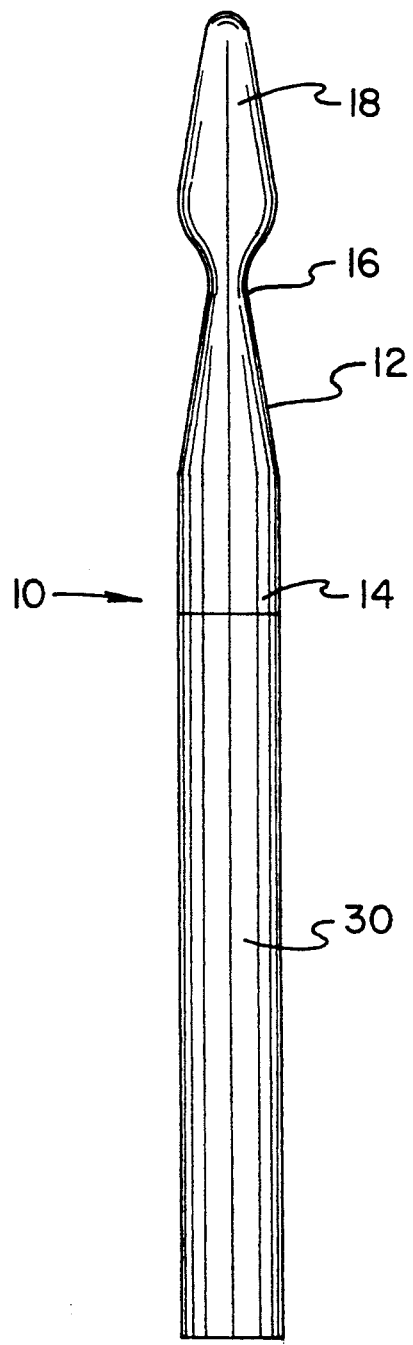
FIG. 1 is a rear elevation view of a toothbrush and dental floss holder comprising the present invention.

With reference now to the drawings, and in particular to FIGS. 1-6 thereof, a new toothbrush and dental floss holder embodying the principles and concepts of the present invention and generally designated by the reference numeral 10 will be described.

From an overview standpoint, the toothbrush and dental floss holder 10 comprises a tapered neck 12 defining a wide end 14 and a narrow end 16. A conventionally shaped toothbrush head 18 is integrally or otherwise fixedly secured to the narrow end 16 of the tapered neck 12, as best illustrated in FIG. 1. The toothbrush head 18 is provided with unillustrated bristles which project therefrom and may be utilized by a user to effect brushing and cleaning of his teeth.

Figure 2:
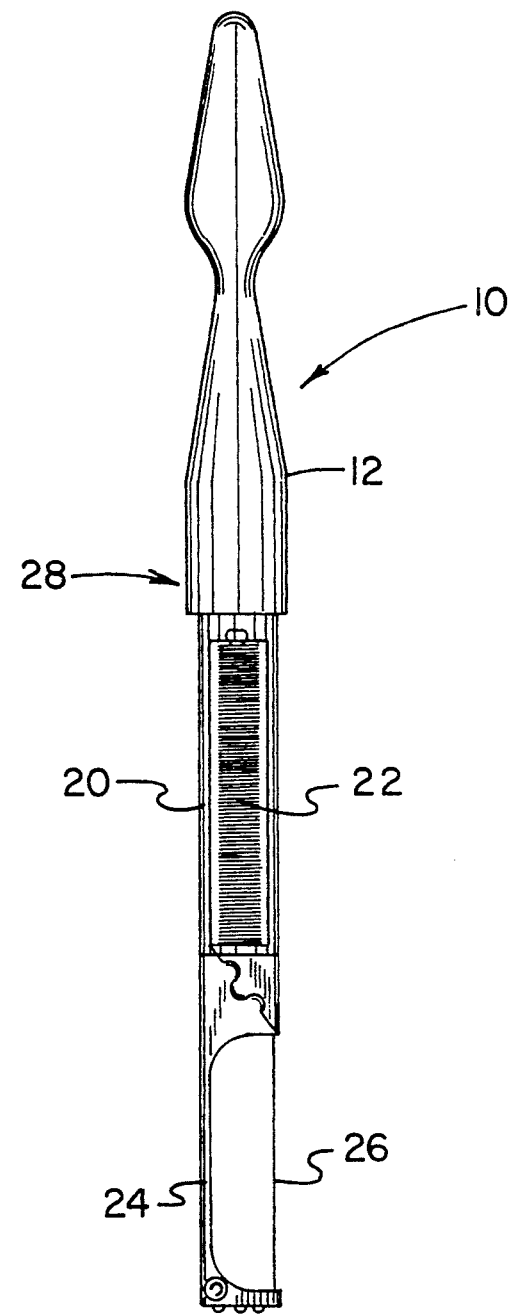
FIG. 2 is a further rear elevation view of the present invention with a component removed.

As best illustrated in FIG. 2, a spool holding frame 20 is integrally or otherwise fixedly secured to the wide end 14 of the tapered neck 12. The spool holding frame 20 supports therewithin a dental floss spool 22 formed of conventional waxed or unwaxed dental floss. Connected to the spool holding frame 20 is a floss holding frame 24 across which a portion of the dental floss 26 may be positioned and held in a taut condition for use thereof by the user. The tapered neck 12, the spool holding frame 20, and the floss holding frame 24 cooperate to define a toothbrush handle 28 which may be grasped and manipulated by the user to effect movement of the toothbrush head 18 within his mouth during use. To protect the floss spool 22 from contamination while the toothbrush is utilized, the spool holding frame 20 and the floss holding frame 24 may be enclosed by a protective cover 30, as shown in FIG. 1.

In use, the toothbrush and dental floss holder 10 provides a convenient means of storing and utilizing dental floss within a toothbrush. The device 10 allows a user to dispense a length of dental floss 26 from the dental floss spool 22, arrange such length across the floss holding frame 24, whereby flossing of the user's teeth may commence. Subsequent to the flossing, the protective cover 30 may be placed over the frames 20, 24, thereby providing a surface against which the user may grasp and manipulate the device 10 to effect cleaning of his teeth with the toothbrush head 18 in a conventional manner.

More specifically, it will be noted that the toothbrush and dental floss holder 10 comprises a handle 28 formed of any substantially resilient plastic material or the like and shaped so as to define a tapered neck 12 having a narrow end 16 from which a toothbrush head 18 integrally projects, as best illustrated in FIG. 1. The tapered neck 12 also defines a wide end 14 from which a spool holding frame 20 longitudinally projects. The handle 28 is completed by a floss holding frame 24 which projects from a lower distal end of the spool holding frame 20 and is longitudinally aligned therewith.

Figure 3:
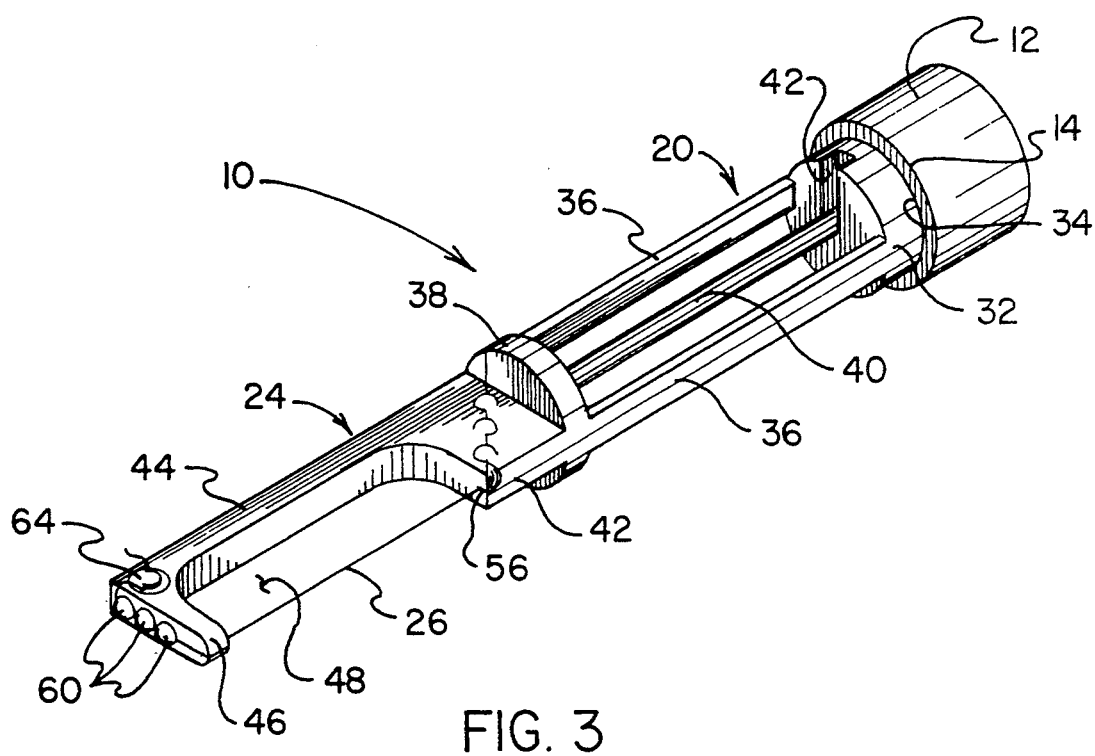
FIG. 3 is a perspective view of a portion of the invention.

Referring now to FIG. 3, it can be shown that the spool holding frame 20 comprises an upper axle mount 32 which is integrally or otherwise fixedly secured to the wide end 14 of the tapered neck 12. The upper axle mount 32 has a diameter slightly less than a diameter of the wide end 14 such that a ridge 34 is defined at a juncture therebetween. Projecting from the upper axle mount in a substantially parallel and spaced relationship to one another, is a pair of side members 36 which are integrally or otherwise fixedly secured to a lower axle mount 38. In this manner, the lower axle mount 38 is supported in a spaced and substantially parallel relationship to the upper axle mount 32 by the side members 36.

Figure 6:
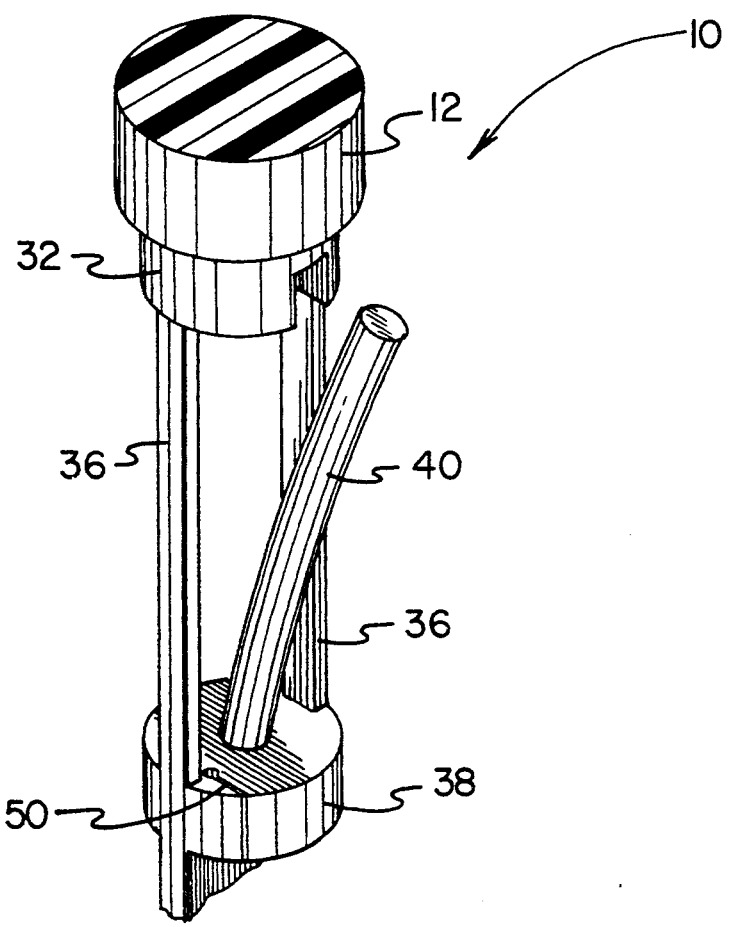
FIG. 6 is an enlarged isometric view detailing the spool holding frame.

A resilient axle 40 extends from the lower axle mount 38 and is received within an axle slot 42 formed into the upper axle mount 32. The axle slot 42 extends from a periphery of the upper axle mount 32 to a center thereof such that the axle 40 may be biased form the axle slot as shown in FIG. 6. This arrangement allows a spool of floss 22 to be positioned concentrically about the axle 40, whereby the resilient tendency of the axle will bias the spool into a parallel relationship with the side members 36 and rotatably support the spool therebetween.

With further reference to FIG. 3, it can be shown that the floss holding frame 24 comprises a substantially rectangularly shaped first end member 42 which is secured to the lower axle mount 38 and which tapers outwardly therefrom to integrally define a bridge member 44. The bridge member 44 integrally continues into a second end member 46 positioned substantially orthogonally with respect to the bridge member and parallel to the first end member 42. In this manner, an opening 48 is defined across which a portion of the dental floss 26 may be suspended.

Figure 5:
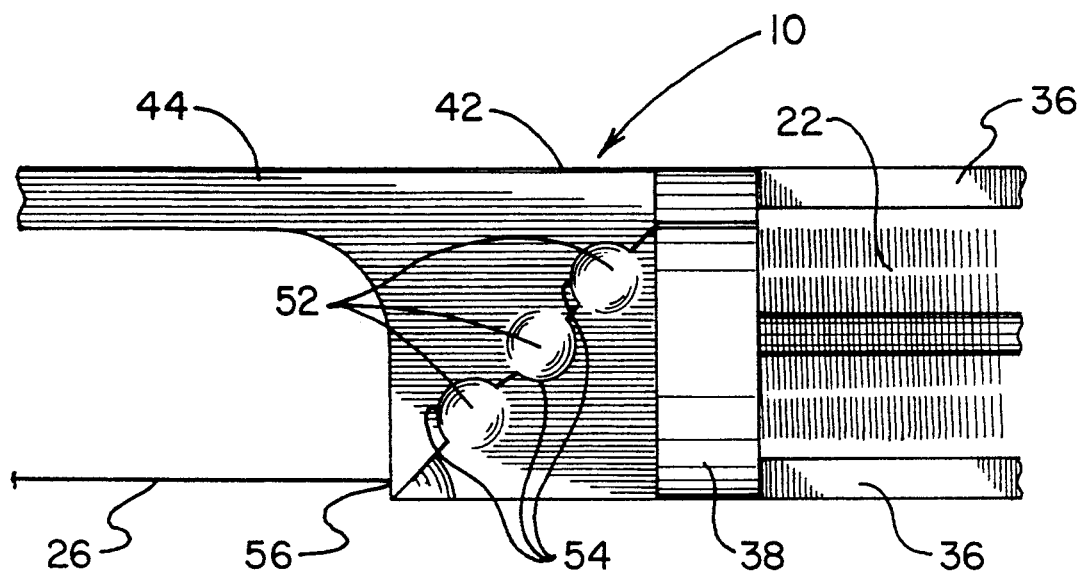
FIG. 5 is an enlarged elevation view of a portion of the invention.

Referring now to FIGS. 5 and 6, it can be shown that the lower axle mount 38 includes a slotted aperture 50 through which dental floss 26 from the dental floss spool 22 may pass. To anchor the dental floss 26 and preclude further dispensing from the spool 22, a plurality of slightly offset slotted projections 52 are provided upon a top area of the first end member 42. The projections 52 are substantially hemispherically shaped and include planar slots 54 oriented in alternating directions. More specifically, the slots 54 are substantially semi-circular and planar in shape and extend in opposite directions within adjacent projections 52. By this structure, the dental floss may be positioned within the slots 54 and held tight by the frictional engagement created thereby.

Figure 4:
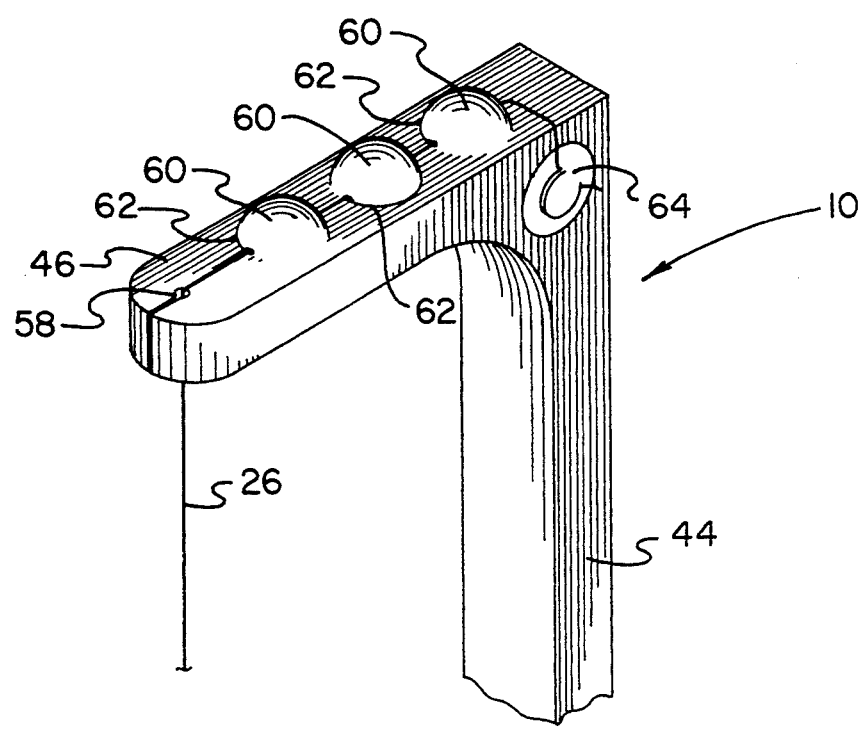
FIG. 4 is an enlarged perspective view of a portion of the invention detailing floss holding means.

As further illustrated in FIG. 5, the dental floss continues from the projections 52 and passes through a slotted aperture 56 within the first end member 42. Turning now to FIGS. 3 and 4, it can be shown that the floss 26 extends through a further slotted aperture 58 in the second end member 46. The slotted apertures 56, 58 are longitudinally aligned and support the floss 26 in a substantially parallel relationship with respect to the bridge member 44.

To anchor the floss 26 to the second end member 46, a further plurality of slotted projections 60 is provided. As similarly taught for the projections 52 of the first end member 42, each of the projections 60 is provided with a planar slot 62 of substantially semi-circular shape, with adjacent projections defining oppositely oriented slots. By this structure, the floss 26 may be secured by the frictional engagement provided between the floss and the projections 60, whereby excess floss may be severed by a floss cutter 64 mounted to the second end member 46.

To complete the handle 28, a protective cover 30 may be axially positioned concentrically over the floss holding frame 24 and the spool holding frame 20, as shown in FIG. 1. The protective cover 30 has an outside diameter substantially equal to the diameter of the wide end 14, and further has an inside diameter of sufficient breadth so that the cover may be positioned over the frames 20, 24, with the ridge 34 permitting a flush engagement of the cover to the neck 12. The cover 30 is retained to the handle 28 by a frictional engagement between the interior surface of the cover and a periphery of the upper axle mount 32.

In use, the toothbrush and dental floss holder 10 provides a convenient means of storing and utilizing dental floss within a toothbrush. The device 10 allows a user to dispense a length of dental floss 26 from the dental floss spool 22, arrange such length across the floss holding frame 24, whereby flossing of the user's teeth may commence. Subsequent to the flossing, the protective cover 30 may be placed over the frames 20, 24, thereby providing a surface against which the user may grasp and manipulate the device 10 to effect cleaning of his teeth with the toothbrush head 18 in a conventional manner.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A toothbrush and dental floss holder comprising:
   tapered neck member having a narrow end and a wide end;
   an upper axle mount secured to said wide end, said upper axle mount being substantially circular and having a perimeter and a center with an axle slot extending from said perimeter to said center thereof;
   a pair of substantially parallel, spaced, elongated side members projecting longitudinally from said upper axle mount;
   a lower axle mount secured to said side members and positioned in a spaced and substantially parallel relationship to said upper axle mount, said lower axle mount having a slotted aperture formed therein;
   an axle projecting from said lower axle mount into said axle slot, said axle being substantially parallelly aligned with said side members, said axle being operable to rotatably support a dental floss spool thereon;
   a first end member fixedly secured to said lower axle member, said end member having a slotted aperture formed therein;
   a bridge member projecting from said first member;
   a second end member fixedly secured to said bridge member and positioned substantially parallel with respect to said first end member, said second end member having a slotted aperture formed therein, said first end member and said bridge member and said second end member cooperating to define an opening across which a length of dental floss may span;
   at least one slotted projection secured to said first end member for anchoring said length of dental floss;
   at least one further slotted projection secured to said second end member for anchoring said length of dental floss; and, a toothbrush head coupled to said narrow end of said neck member, wherein said at least one slotted projection comprises three projections colinearly arranged, each of said projections having a semi-circular, planar slot formed therein for receiving a portion, of said length of dental floss, said semi-circular planar slots extending in opposite directions with respect to adjacent projections.

2. The toothbrush and dental floss holder of claim 1, wherein said at least one further slotted projection comprises three further projections colinearly arranged, each of said further projections having a semi-circular, planar slot formed therein for receiving a portion of said length of dental floss, said semi-circular planar slots extending in opposite directions with respect to adjacent further projections.

3. The toothbrush and dental floss holder of claim 2, and further comprising a floss cutter secured to said holder.

4. The toothbrush and dental floss holder of claim 3, and further comprising a cover which may be axially and concentrically positioned over said upper axle mount to frictionally engage therewith.

5. The toothbrush and dental floss holder of claim 4, wherein said axle is formed of a substantially resilient material.

6. The toothbrush and dental floss holder of claim 5, wherein said toothbrush and dental floss holder is integrally molded from a substantially resilient plastic material.

* * * * *